United States Patent [19]

Farquharson et al.

[11] Patent Number: 4,639,267
[45] Date of Patent: Jan. 27, 1987

[54] HERBICIDAL CYCLOHEXANE-1,3-DIONE DERIVATIVES

[75] Inventors: Graeme J. Farquharson, Carlton; Keith G. Watson, Blackburn North; Graham J. Bird, Ascot Vale, all of Australia

[73] Assignee: ICI Australia Limited, Victoria, Australia

[21] Appl. No.: 774,526

[22] Filed: Sep. 10, 1985

[30] Foreign Application Priority Data

Sep. 24, 1984 [AU] Australia ............................ PG7274

[51] Int. Cl.⁴ .................... A01N 35/10; C07C 131/00
[52] U.S. Cl. ....................................... 71/98; 564/257; 71/103; 71/105; 71/106; 71/107; 71/121; 558/48; 558/426; 560/10; 560/20; 560/22; 560/23; 560/35; 560/64; 560/65; 560/255
[58] Field of Search .................... 564/257; 560/10, 35, 560/20, 22, 23, 64, 65; 260/465 E; 71/98, 103, 105, 106, 107, 121; 558/48, 426

[56] References Cited

FOREIGN PATENT DOCUMENTS 124992 11/1984 European Pat. Off. ............ 564/257

Primary Examiner—Natalie Trousof
Assistant Examiner—L. Hendriksen
Attorney, Agent, or Firm—Cushman, Darby & Cushman

[57] ABSTRACT

The invention concerns novel compounds of the formula I and isomers thereof

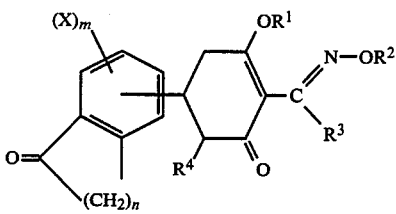

wherein:
n is an integer selected from 2 to 4;
m is zero or an integer selected from 1 to 3;
X, which may be the same or different, are independently selected from halogen, alkyl, alkoxy and alkylthio;
$R^1$ is selected from hydrogen, acyl and an inorganic or organic cation;
$R^2$ is selected from alkyl, substituted alkyl, alkenyl, haloalkenyl, alkynyl and haloalkynyl;
$R^3$ is selected from alkyl, fluoroalkyl, alkenyl, alkynyl, and phenyl; and
$R^4$ is selected from hydrogen, halogen, alkyl, cyano and alkoxycarbonyl.

The compounds of the invention show herbicidal properties and plant growth regulating properties and in further embodiments the invention provides processes for the preparation of compounds of formula I, intermediates useful in the preparation of the compounds of the formula I, compositions containing as active ingredient a compound of formula I, and herbicidal and plant growth regulating processes utilizing compounds of formula I.

12 Claims, No Drawings

HERBICIDAL CYCLOHEXANE-1,3-DIONE DERIVATIVES

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes utilizing such compounds.

The use of certain cyclohexane-1,3-dione derivatives as grass herbicides is known in the art. For example, the "Pesticide Manual" (C. R. Worthing Editor, The British Crop Protection Council, 6th Edition 1979) describes the cyclohexane-1,3-dione derivative known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Australian Pat. No. 464 655 and its equivalents such as U.K. Pat. No. 1 461 170 and U.S. Pat. No 3,950,420.

More recently, at the 1980 British Crop Protection Conference ("1980 British Crop Protection Conference-Weeds, Proceedings Vol 1, Research Reports", pp 39 to 46, British Crop Protection Council, (1980), a new cyclohexane-1,3-dione grass herbicide code named NP 55 (2-N-ethoxybutrimidoyl)-5-(2-ethylthiopropyl)-3-hydroxy-2-cyclohexen-1-one) was announced. This compound is disclosed in Australian Pat. No. 503 917 and its equivalents.

From European Patent Application Ser. No. 086 588, it is also known that 5-indanyl- and 5-tetralinylcyclohexane-1,3-dione derivatives exhibit useful herbicidal properties. It has now been found that a new group of 5-(oxoindanyl or oxotetralinyl) cyclohexane-1,3-dione derivatives exhibit particularly strong general grass-killing properties.

Accordingly the invention provides a compound of formula I or an isomer thereof:

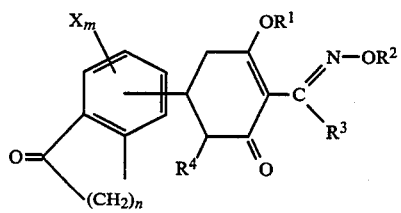

I wherein:
n is an integer selected from 2 to 4;
m is zero or an integer selected from 1 to 3;
X, which may be the same or different, are independently selected from the group consisting of: halogen; $C_1$ to $C_6$ alkyl; $C_1$ to $C_6$ alkoxy; and $C_1$ to $C_6$ alkylthio;
$R^1$ is selected from the group consisting of: hydrogen; an acyl group; and an inorganic or organic cation;
$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_3$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, $C_1$ to $C_6$ alkyl, $C_1$ to $C_6$ haloalkyl, $C_1$ to $C_6$ alkoxy, $C_1$ to $C_6$ alkylthio;

$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and $R^4$ is selected from the group consisting of: hydrogen; halogen; $C_1$ to $C_6$ alkyl; cyano; and ($C_1$ to $C_6$ alkoxy) carbonyl.

When in the compound of formula I $R^1$ is chosen from acyl the nature of the acyl group is not narrowly critical. Although not intending to be bound by theory, it is believed that when $R^1$ is acyl the acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkythio.

When in the compound of formula I $R^1$ is chosen from an inorganic or organic cation the nature of the cation is not narrowly critical. Although not intending to be bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^9R^{10}R^{11}R^{12}N^+$ wherein $R^9$, $R^{10}$, $R^{11}$ and $R^{12}$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R^1$ is hydrogen the compounds of the invention may exist in any one of four tautomeric forms as shown below wherein $\phi$ represents the group

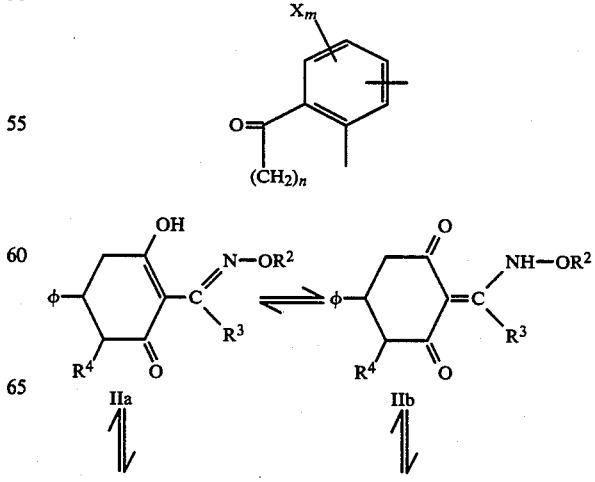

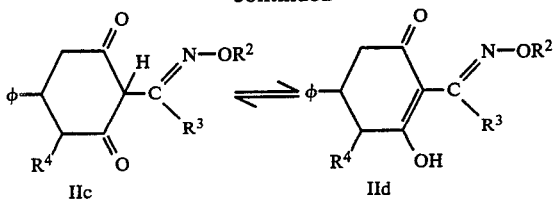

The compounds of the invention include: indanone derivatives of formula Ia; and

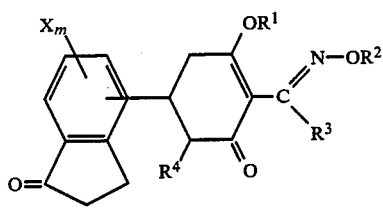

tetralone derivatives of formula Ib.

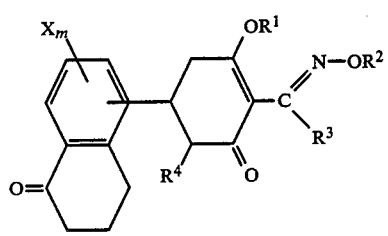

Preferred compounds of the invention include those compounds of formula I wherein:

n is an integer selected from 2 and 3;

m is an integer selected from 1 to 3;

X, which may be the same or different, are independently selected from the group consisting of: halogen; $C_1$ to $C_6$ alkyl; $C_1$ to $C_6$ alkoxy; and $C_1$ to $C_6$ alkylthio;

$R^1$ is selected from the group consisting of: hydrogen; $C_2$ to $C_6$ alkanoyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy; benzenesulfonyl and substituted benzenesulfonyl wherein the benzene ring is substituted with from one to three substituents selected from the group consisting of halogen, nitro, $C_1$ to $C_6$ alkyl and $C_1$ to $C_6$ alkoxy; and an inorganic or an organic cation selected from the alkali metals such as lithium, potassium and sodium, the alkaline earth metals such as magnesium, calcium and barium, the transition metals such as manganese, copper, zinc, iron, nickel, cobalt and silver, the ammonium ion and the tri- and tetra- (alkyl)ammonium ions wherein alkyl is selected from $C_1$ to $C_6$ alkyl and $C_1$ to $C_6$ hydroxyalkyl;

$R^2$ is selected from the group consisting of $C_1$ to $C_6$ alkyl, $C_2$ to $C_6$ alkenyl, $C_2$ to $C_6$ alkynyl, $C_1$ to $C_6$ haloalkyl, $C_2$ to $C_6$ halo alkenyl and $C_3$ to $C_6$ haloalkynyl;

$R^3$ is selected from $C_1$ to $C_6$ alkyl; and $R^4$ is hydrogen.

More preferred compounds of the invention include those compounds of formula I wherein:

n is an integer selected from 2 and 3;

m is an integer selected from 1 to 3;

X, which may be the same or different, are independently selected from the group consisting of: chlorine; methyl; methoxy; and methylmercapto;

$R^1$ is selected from the group consisting of hydrogen, benzoyl and the alkali metals;

$R^2$ is selected from the group consisting of $C_1$ to $C_6$ alkyl, $C_1$ to $C_6$ haloalkyl, $C_2$ to $C_6$ alkenyl and $C_2$ to $C_6$ alkynyl;

$R^3$ is selected from the group consisting of $C_1$ to $C_6$ alkyl; and $R^4$ is hydrogen.

Even more preferred compounds of the invention include those compounds of formula I wherein:

n is an integer selected from 2 and 3;

m is an integer selected from 1 to 3;

X, which may be the same or different, are independently selected from the group consisting of: chlorine; methyl; methoxy; and methylmercapto;

$R^1$ is selected from the group consisting of hydrogen and alkali metals;

$R^2$ is selected from the group consisting of $C_1$ to $C_3$ alkyl; $C_1$ to $C_3$ fluoroalkyl; allyl; and propargyl;

$R^3$ is selected from the group consisting of $C_1$ to $C_3$ alkyl; and $R^4$ is hydrogen.

Examples of compounds embraced by the invention include:

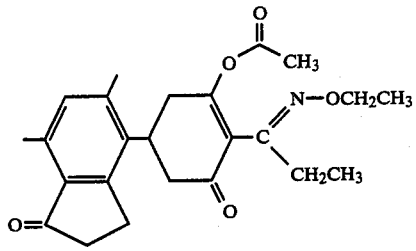

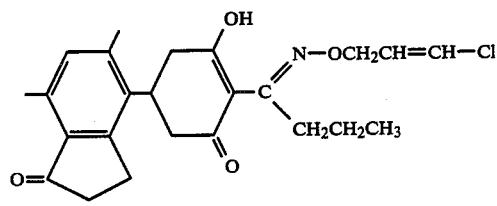

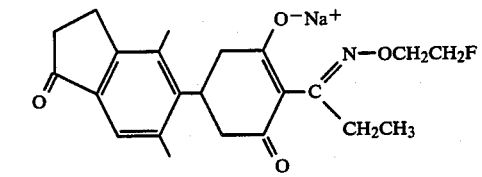

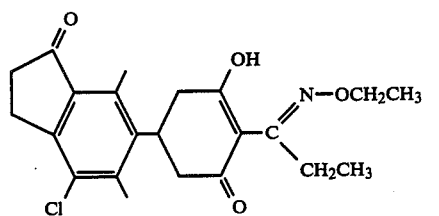

-continued

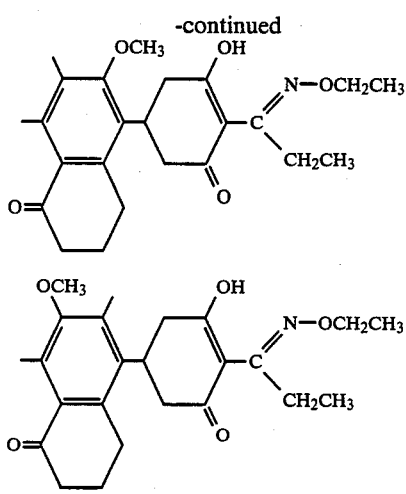

Specific examples of the compounds of the invention includes the compounds listed in Table 1 below:

TABLE 1

| Compound No | (X)m | Position of ring linkage | $R^1$ | $R^2$ |
|---|---|---|---|---|
| 7 | 5,7-$(CH_3)_2$ | 4 | H | $CH_2CH_3$ |
| 8 | 5,7-$(CH_3)_2$ | 6 | H | $CH_2CH_3$ |
| 9 | 5,7-$(CH_3)_2$ | 4 | H | $CH_2CH=CH_2$ |
| 10 | 5,7-$(CH_3)_2$ | 6 | H | $CH_2CH=CH_2$ |
| 11 | 5,7-$(CH_3)_2$ | 4 | Na | $CH_2CH_3$ |

The compounds of the invention may be prepared by a variety of methods and in a further aspect the invention provides methods for the preparation of compounds of formula I.

Conveniently the preparation of the compounds of the invention can be considered in four or five parts.

Part A involves the formation of a 5-arylcyclohexan-1,3-dione of formula IX. This reaction may be carried out in a two step process by:

(i) reacting, preferably in the presence of a base, an aldehyde derivative of formula V with acetone (IVa) or an acetone derivative of formula IVb to form a ketone derivative of formula VIa or VIb respectively; and reacting, preferably in the presence of a base, a ketone derivative of formula VIa with a malonic acid ester derivative of formula VIIa or a ketone derivative of formula VIb with a malonic acid ester of formula VIIb, to give an intermediate of formula VIIIa or VIIIb respectively which may be isolated or hydrolysed directly, preferably in the presence of an acid, to give a 5-arylcyclohexan-1,3-dione of formula IX, or reacting, preferably in the presence of a base, a ketone derivative of formula VIa with an alkanoic acid ester of formula VIIc to give a 5-arylcyclohexan-1,3dione of formula IX;

(ii) reacting, preferably in the presence of a base, an aldehyde derivative of formula V with a malonic acid ester of formula VIIb to give an arylmethylidenemalonate derivative of formula VIc which is in turn reacted, preferably in the presence of a base, with an acetoacetic acid derivative of formula VIId to give an intermediate of formula VIIIc which may be isolated or hydrolysed directly, preferably in the presence of an acid, to give a 5-arylcyclohexan-1,3-dione of formula IX;

(iii) reacting, preferably in the presence of a base, an aldehyde derivative of formula V with an acetic acid ester of formula IVc to give a 2-arylalkenoate derivative of formula VId which is in turn reacted, preferably in the presence of a base, with an acetoacetic acid ester derivative of formula VIId to give an intermediate of formula VIIIa which may be isolated or hydrolysed directly, preferably in the presence of an acid, to give a 5-arylcyclohexan-1,3-dione of formula IX, or (iv) reacting an aldehyde derivative of formula V with an ylide of formula IVd or IVe, wherein Ar is an aryl group, to form a derivative of formula VIa or VId respectively; and further reaction of the derivatives of formula VIa or VId as described above in parts (i) and (iii) respectively to give a 5-arylcyclohexan-1,3dione of formula IX.

Part B involves reaction of a 5-arylcyclohexan-1,3-dione of formula IX with an acidic dehydrating agent to give a derivative of formula X. Suitable dehydrating agents include polyphosphoric acid and methanesulfonic acid.

Part C involves the acylation of a compound of formula X to give a 2-acyl-5-arylcyclohexan-1,3-dione derivative of formula XIV. The acylation reaction may be carried out by reacting a derivative of formula X with:

(v) an acid anhydride of formula XI in the presence of either an alkali metal salt of the corresponding acid of formula XII or an alkoxide salt of formula XIII, wherein M is an alkali metal ion and R is $C_1$ to $C_6$ alkyl;

(vi) an acid anhydride of formula XI in the presence of the corresponding acid of formula XV, preferably in the presence of a Lewis acid or Bronsted acid catalyst;

(vii) an alkali or alkaline earth metal hydride followed by reaction with an acid anhydride of formula XI or an acid halide of formula XVI;

(viii) an acid anhydride of formula XI in the presence of a strong organic base such as 4-dimethylaminopyridine or imidazole. Alternatively, this reaction may be carried out by:

(ix) reacting a derivtive of formula X with an acid halide of formula XVI in the presence of a base to give an intermediate O-acyl derivative of formula XVII; and (x) reacting the intermediate of formula XVII with a Lewis acid or Bronsted acid catalyst;

(xi) reacting the intermediate of formula XVII with a suitable strong organic base such as 4-dimethylaminopyridine or imidazole.

Part D involves the formation of a compound of the invention of formula I wherein $R^1$ is hydrogen, that is a compound of formula II. This reaction may be carried out either by reacting a 2-acyl-5-arylcyclohexane-1,3-dione derivative of formula XIV with:

(xii) an alkoxyamine derivative of formua XVIII, or
(xiii) hydroxylamine to give an intermediate oxime derivative of formula XIX and reacting that intermediate oxime derivative of formula XIX with an alkylating agent of formula XX, wherein L is a leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

Part E involves the formation of a compound of the invention of formula I where $R^1$ is a substituent other than hydrogen.

Compounds of the invention of formula I, wherein $R^1$ forms an acyl or sulfonyl derivative of a compound of formula II, may be prepared from the corresponding compounds of the invention of formula II by reacting with an acylation or sulfonylation reagent of formula XXI.

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, as hereinbefore defined, which process comprises:

reacting 2-acyl-5-arylcyclohexane-1,3-dione derivative of formula XIV with an alkoxyamine derivative of formula XVIII to give a compound of the invention of formula II or reacting the 2-acyl-5-arylcyclohexane-1,3-dione derivative of formula XIV with hydroxylamine and alkylating the oxime intermediate of formula XIX with an alkylating agent of formula XX, wherein L is a leaving group, to give a compound of the invention of formula II; and optionally reacting the compound of the invention of formula II with a compound of formula XXI wherein L is a leaving group, to give a compound of the invention of formula I.

Certain of the intermediate compounds of formulae VI, VIII, IX, X, XIV, XVII and XIX are novel compounds and therefore in further embodiments the invention provides novel compounds of formulae VI, VIII, IX, X, XIV, XVII and XIX and processes for the preparation thereof.

It is not possible to use standard methods such as the Vilsmeier formylation or dichloromethyl methyl ether to prepare formylindanones or formyltetralones which would be the expected starting materials for the preparation of the cyclohexan-1,3-diones of formula X. It was necessary to find a means of forming the indanone or tetralone ring system after the cyclohexane-1,3-dione ring formation.

Accordingly, in a further aspect the invention provides a process for the preparation of 5-(1-oxoindanyl)- and 5-(1-oxotetrahydronaphthyl) cyclohexan-1,3-dione derivatives of formula X, which process comprises reacting a 5-(carboxyalkyl phenyl) cyclohexan-1,3-dione of formula IX with an acidic dehydrating agent.

The structures of the compounds described above are detailed on the following pages wherein $\phi$ represents the group.

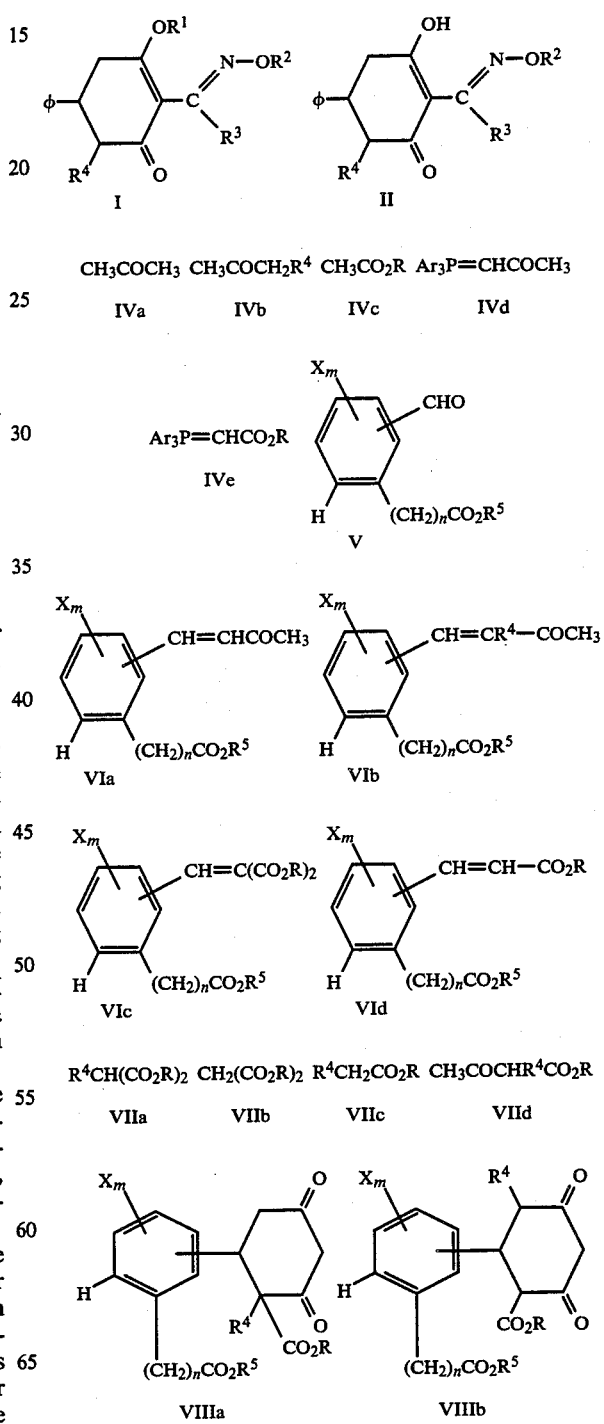

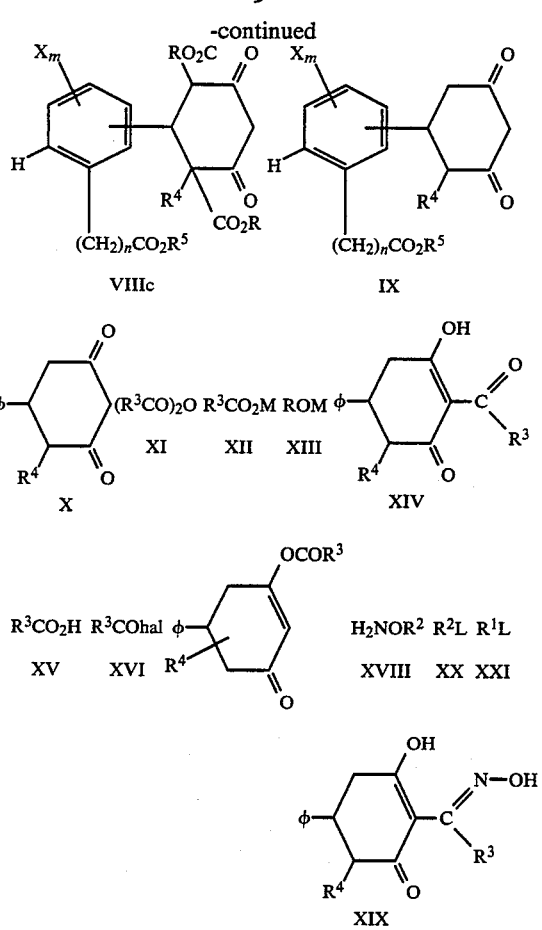

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are selectively active against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to control monocotyledonous weeds in cultivated crops, especially wild grasses in cereal crops. Certain of such compounds of the invention are especially useful in the control of wild grasses such as wild oats and rye grass in crops of cultivated monocotyledonous plants such as wheat, barley and other varieties of cereals.

Accordingly, in yet a further aspect the invention provides a process for controlling monocotyledonous weeds in cultivated crops, especially wild grasses in cereal crops such as wheat, which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (preemergence application). However, the compounds are, in general, more effective when applied to the plant postemergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides growth inhibiting, plant damaging, or plant killing compositions comprising a compound of formula I as hereinbefore defined and an inert carrier therefor.

Certain of the compounds of formula I exhibit useful plant growth regulating activity. For example, while compounds of formula I are selectively active herbicides against wild grasses in crops of cultivated plants at some rates of application they exhibit plant growth regulating effects in said crops.

Plant growth regulating effects may be manifested in a number of ways. For example, suppression of apical dominance, stimulation of auxiliary bud growth, stimulation of early flowering and seed formation, enhancement of flowering and increase in seed yield, stem thickening, stem shortening and tillering. Plant growth regulating effects shown in compounds of the invention may include, for example, tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acids, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersions of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compostions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 10 to 99%, preferably 10 to 60%, by weight of active ingredient.

Emulsion or emulsifiable concentrates are conveniently prepared by dissolving the active ingredient in an organic solvent containing one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active agent and preferably at least one suspending agent. Suitable suspending agents include: hydrophilic colloids such as, for example, poly(N-vinylpyrrolidone), sodium carboxymethylcellulose and the vegetable gums, gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectate is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Example of useful complementary herbicides include:

A. benzo-2,1,3,-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4-dichlorophenoxy acetic acid (common name 2,4,-D) 2,4,5-trichlorophenoxyacetic acid (common name 2,4,5-T), 4-(4-chloro-2-methylphenoxy)butyric acid (common name MCPB), 4-(2,4-dichlorophenoxy)butyric acid (common name 2,4-DB), 2-(4-chloro-2-methylphenoxy)propionic acid (common name mecoprop), and their derivatives (e.g. salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (e.g. acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N, N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)-carbamate (common name phenmedipham) and 3-[(ethoxycarbonylamino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine). 2-chloro-4,6-di(ethylamino)-1,3,5-triazine (common name simazine) and 2-azido-4-(isopropylamino)-6-methylthio-1,3,5-triazine (common name aziproptryne);

K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. pyridine herbicides such as 3,6-dichloropicolinic acid (common name clopyralid) and 4-amino-3,5,6-trichloropicolinic acid (common name picloram);

M. 1,2,4-triazin-5-one herbicides such as 4-amino-4,5-dihydro-3-methyl-6-phenyl-1,2,4-triazine-5-one (common name metamitron) and 4-amino-6-tert-butyl 4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben);

O. anilide herbicides such as N-butoxymethyl-α-chloro-2',6'-diethylacetanilide (common name butachlor), the corresponding N-methoxy compound (common name alachlor), the corresponding N-isopropyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189);

T. Aryloxyphenoxypropionate herbicides such as butyl 2-[4-(5-trifluoromethyl-2-pyridyloxy)phenoxy]propionate (common name fluazifop) and methyl 2-[4-(2,4-dichlorophenoxy)phenoxy]propionate (common name diclofop); and U. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

V. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

W. organoarsenical herbicides such as monosodium methanearsonate (common name MSMA); and X. amino acid herbicides such as N-(phosphonomethyl)glycine (common name glyphosate) and its salts and esters.

The invention is now illustrated by but in no way limited to the following example.

EXAMPLE 1

5-(6,8-Dimethyl-7-methoxy-1-oxo-1,2,3,4-tetrahydronaphth-5-yl)-2-[1-(ethoxyimino)propyl]-3-hydroxycyclohex-2-en-1-one (6)

(i) Succinic anhydride (22.06 gm) was added to a mixture of 2,6-dimethylanisole (30 g) and anhydrous aluminium trichloride (59 g) in 1,2-dichloroethane (200 ml) at 0° C. The mixture was stirred for 0.5 hr at 0° C. and at room temperature for 4 hr. The mixture was poured onto ice-concentrated hydrochloric acid. After stirring vigorously for 5 min, the mixture was extracted with ethyl acetate. The dried ($MgSO_4$) organic fraction was evaporated to give 4-(3,5-dimethyl-4-methoxyphenyl)-4-oxobutyric acid as white crystals, mp 108° C.

(ii) A mixture of 4-(3,5-dimethyl-4-methoxyphenyl)-4-oxobutyric acid (13 g), zinc amalgam [prepared from zinc (15 g) and mercuric chloride (1.5 g)], glacial acetic acid (70 ml), water (70 ml) and concentrated hydrochloric acid (170 ml) was heated at reflux for 12 hr. The cooled mixture was filtered and the filtrate was poured into water (1 liter). The mixture was extracted with ethyl acetate and the organic fraction was washed four times with water. The dried ($MgSO_4$) organic fraction was evaporated to give 4-(3,5-dimethyl-4-hydroxyphenyl)-butyric acid as a pale yellow oil. Pmr spectrum ($CDCl_3$; δ in ppm): 1.79–2.64 (6H,m); 2.22 (6H,s); 6.79 (2H,s); 7.6 (2H,brs).

(iii) Dimethyl sulfate (6 ml) was added to a well stirred mixture of 4-(3,5-dimethyl-4-hydroxyphenyl)butyric acid (9.4 g) and sodium hydroxide (2.69 g) in water (150 ml) at 5°–10° C. The mixture was stirred for 20 mins at 10° C. and was then heated to reflux for 1 hr. The cooled mixture was poured into water (200 ml) which was then extracted with diethyl ether. The dried ($MgSO_4$) organic fraction was evaporated to give methyl 4-(3,5-dimethyl-4-methoxyphenyl)butyrate as a pale yellow oil. Pmr spectrum ($CDCl_3$; δ in ppm): 1.89–2.61 (6H,m); 2.25 (6H,s); 3.66 (3H,s); 3.69 (3H,s); 6.81 (2H,s).

(iv) Dichloromethyl methyl ether (5.3 g equiv) was added slowly to a well stirred mixture of methyl 4-(3,5-dimethyl-4-methoxyphenyl)butyrate (9.75 g) and titanium tetrachloride (31 g equiv) in dichloromethane (200 ml) at 0°–5° C. The mixture was stirred for 1 hr at 5° C. and at room temperature for 2 hrs. The mixture was poured onto ice-water which was then extracted with dichloromethane. The dried ($MgSO_4$) organic fraction was evaporated to give methyl 4-(3,5-dimethyl-2-formyl-4-methoxyphenyl)butyrate as a pale yellow oil. Pmr spectrum ($CDCl_3$; δ in ppm): 1.69–2.98 (6H,m); 2.31 (3H,s); 2.52 (3H,s); 3.67 (3H,s); 3.69 (3H,s); 6.91 (1H,s); 10.50 (1H,s).

(v) Methyl 4-(3,5-dimethyl-2-formyl-4-methoxyphenyl)butyrate (9.4 g) and 1-triphenylphosphoranylidene-2-propanone (21 g equiv) were heated and stirred at reflux in toluene for 48 hr. The solvent was evaporated under reduced pressure and the residue was purified by column chromatography over silica with dichloromethane elution to give methyl 4-[2-(but-1-en-3-one-1-yl)-3,5-dimethyl-4-methoxyphenyl]butyrate as a pale yellow oil. Pmr spectrum ($CDCl_3$; δ in ppm): 1.83–2.69 (6H,m); 2.25 (3H,s); 2.28 (3H,s); 2.41 (3H,s); 3.66 (3H,s); 3.70 (3H,s); 6.26 (1H,d); 6.89 (1H,s); 7.65 (1H,d).

(vi) Methyl 4-(2-(but-1-en-3-one-1-yl)-3,5-dimethyl-4-methoxyphenyl)butyrate (5.0 g) and sodium dimethyl malonate (6 g equiv) were stirred and heated at reflux in dry methanol (60 ml) for 6 hr. The solvent was evaporated under reduced pressure and the residue was heated at reflux with a 10% excess of an aqueous potassium hydroxide solution (60 ml) for 8 hr. The cooled mixture was extracted with diethyl ether. The aqueous fraction was heated to 60° C. and was acidified by slow addition of a dilute aqueous hydrochloric acid solution. The cooled mixture was extracted with ethyl acetate. The dried ($MgSO_4$) organic fraction was evaporated to give 5-(6-[3-(carboxy)propyl]-2,4-dimethyl-3-methoxyphenyl)-3-hydroxycyclohex-2-en-1-one as a pale yellow foam. Pmr spectrum (acetone-$d_6$; δ in ppm): 1.6–3.7 (11H,m); 2.28 (3H,m); 2.43 (3H,s); 3.65 (3H,s); 5.52 (1H,s); 6.91 (1H,s); 8.6 (2H,brs).

(vii) 5-(6-[3-(Carboxy)propyl]-2,4-dimethyl-3-methoxyphenyl)-3-hydroxycyclohex-2-en-1-one (4.0 g) was slowly heated and stirred in polyphosphoric acid from 80° C. to 140° C. (bath temperature) over 1.5 hr. The cooled mixture was poured onto ice-water and was then extracted with ethyl acetate. The dried ($MgSO_4$) organic fraction was evaporated to give 5-(6,8-dimethyl-7-methoxy-1-oxo-1,2,3,4-tetrahydronaphth-5-yl)-3-hydroxycyclohex-2-en-1-one as a pale yellow foam.

(viii) A mixture of 5-(6,8-dimethyl-7-methoxy-1-oxo-1,2,3,4-tetrahydronaphth-5-yl)-3-hydroxycyclohex-2-en-1-one (1.0 g) and propionic anhydride (2 ml) was stirred and heated at reflux in toluene (80 ml) for 1 hr. The solvent was evaporated and the residue was heated under high vacuum to remove excess anhydride. The residue was then heated at reflux with dimethylaminopyridine (0.2 g) in toluene (80 ml) for 8 hr. The solvent was evaporated and the residue was purified by column chromatography over silica with dichloromethane/ethyl acetate (9:1 v/v) elution to give 5-(6,8-dimethyl-7-methoxy-1-oxo-1,2,3,4-tetrahydronaphth5-yl)-3-hydroxy-2-propionylcyclohex-2-en-1-one as a pale yellow oil. Pmr spectrum ($CDCl_3$; δ in ppm): 1.17 (3H,t); 1.7–3.7 (13H,m); 2.41 (3H,s); 2.52 (3H,s); 3.66 (3H,s); 18.28 (1H,s).

(ix) A mixture of 5-(6,8-dimethyl-7-methoxy-1-oxo-1,2,3,4-tetrahydronaphth-5-yl)-3-hydroxy-2-propionylcyclohex-2-en-1-one (0.48 g), ethoxyamine hydrochloride (1 equiv), anhydrous sodium acetate (1 equiv) and absolute alcohol (30 ml) was stirred at room temperature for 1 hr. The mixture was poured into a very dilute aqueous hydrochloric acid solution which was then immediately extracted with diethyl ether. The dried (MgSO$_4$) organic fraction was evaporated to give 5-(6,8-dimethyl-7-methoxy-1-oxo-1,2,3,4-tetrahydronaphth-5-yl)-2[1-(ethoxyimino)propyl]-3-hydroxycyclohex-2-en-1-one (6) as a pale yellow oil. Pmr spectrum (CDCl$_3$; δ in ppm): 1.11–1.42 (6H,2xt); 1.9–3.8 (15H,m); 2.41 (3H,s); 2.52 (3H,s); 3.66 (3H,s); 4.14 (2H, q); OH not observed.

EXAMPLE 2

5-(5,7-Dimethyl-1-oxoindan-4-yl)-2-[1-(ethoxyimino)propyl]cyclohexane-1,3-dione (7) and 5-(5,7-dimethyl-1-oxoindan-6-yl)-2-[1-(ethoxyimino)propyl]cyclohexane-1,3-dione (8).

(i) A mixture of 3,5-dimethyl benzyl bromide (1 g), anhydrous potassium carbonate (0.69 g) and dimethylmalonate (0.57 ml) in dimethylfomamide (2.5 ml) was stirred overnight at room temperature. The mixture was poured into dilute hydrochloric acid and extracted with methylene chloride. The organic layer was washed with water, then dried (MgSO$_4$) and evaporated to a colourless oil (1.0 g) which was identified as dimethyl 3,5-dimethylbenzylmalonate.

(ii) A mixture of dimethyl 3,5-dimethybenzlmalonate (11.4 g, 46 m mol) and bonc acid (5.6 g, 92 m mol) was heated with stirring at 180° C. for 3 hours. After cooling the mixture was dissolved in diethyl ether and water and the organic layer was dried (MgSO$_4$) and evaporated to give a brown oil (8.6 g) which was identified as methyl 3-(3,5-dimethylphenyl)propionate. Proton magnetic resonance spectrum (CDCl$_3$; δ in ppm); 2.31 (6H, S); 2.70 (4H, d of d); 3.66 (3H, s); 6.77 (3H, s).

(iii) Methyl 3-(3,5-dimethylphenyl) propionate was converted into a mixture of two isomeric 5-(5,7-dimethyl-1-oxoindanyl)-2-propionylcyclohexane-1,3-diones following essentially the same procedure as described in Example 1 parts (iv) to (viii). Column chromatography of the crude mixture of isomers using silica gel as adsorbent and eluting with methylene chloride allowed the separation of the pure isomers. The faster moving trione was assigned the structure 5-(5,7-dimethyl-1-oxoindan-6-yl)-2-propionylcyclohexane-1,3-dione based on its proton magnetic resonance spectrum (CDCl$_3$; δ in ppm): 1.16 (3H, t); 2.48 (3H,s); 2.75 (3H,s); 2.3–4.0 (11H, m); 7.14 (1H, s); 18.28 (1H,s).

(iv) Each of the separated isomeric 5-(5,7-dimethyl-1-oxoindanyl)-2-propionylcyclohexane-1,3-diones from part (iii) was reacted with ethoxyamine following the general procedure described in Example 1 part (ix).

5-(5,7-Dimethyl-1-oxoindan-4-yl)-2-[1-(ethoxyimino)propyl]cyclohexane-1, 3-dione (7) was isolated as a pale yellow oil, proton magnetic resonance spectrum (CDCl$_3$; δ in ppm): 1.17 (3H,t); 1.34 (3H,t); 2.43 (3H,s); 2.55 (3H,s); 2.3–4.0 (11 H,m); 4.12 (2H,q); 6.88 (1H,s); 15.0 (1H,bs).

5-(5,7-Dimethyl-1-oxoindan-6-yl)-2-[1-(ethoxyimino propyl]cyclohexane-1,3-dione (8) was isolated as a pale yellow oil, proton magnetic resonance spectrum (CDCl$_3$; δ in ppm): 1.18 (3H,t ; 1.34 (3H,t); 2.47 (3H,s); 2.73 (3H,s); 2.4–4.0 (11H,m); 4.13 (2H,q); 7.08 (1H,s); 15.1 (1H,bs).

EXAMPLE 3

A mixture of the isomeric 5-(5,7-dimethyl-1-oxoindan-4-(and-6-) yl)-2-propionylcyclohexane-1,3-diones from Example 2 part (iii) was reacted with allyloxyamine following the general procedure described in Example 1 part (ix).

A mixture of 2-[1-(allyloxyimino)propyl]-5-(5,7-dimethyl-1-oxoindan-4-yl)cyclohexane-1,3-dione (9) and 2-[1-(allyloxyimino)propyl]-5-(5,7-dimethyl-1-oxoindan-6-yl)cyclohexane-1,3-dione (10) was obtained as a pale yellow oil, proton magnetic resonance spectrum (CDCl$_3$; δ in ppm): 1.18 (3H,t); 2.44 (approx 2H,s); 2.55 (approx 2H,s); 2.46 (approx 1H,s); 2.74 (approx 1H,s); 2.3–3.4 (10H,m); 3.5–4.0 (1H,m); 4.52 (2H,d); 5.15 (2H,m); 6.0(1H,m); 6.90 (0.7H,s); 7.08 (0.3H,s); 15.0 (1H,bs).

EXAMPLE 4

Sodium salt of 5-(5,7-dimethyl-1-oxoindan-4-yl)-2-[1-(ethoxyimino)propyl]cyclohexane-1,3-dione (11).

A solution of sodium hydroxide (4 mg, 0.1 m mol) in water (0.5 ml) was added to a solution of 5-(5,7-dimethyl-1-oxoindan-4-yl)-2-[1-(ethoxyimino)propyl]cyclohexane-1,3-dione (7) (37 mg, 0.1 m mol) in acetone (2 ml). The mixture was stirred at room temperature briefly and then evaporated to dryness under reduced pressure. Final traces of water were removed by azeotropic distillation with toluene. The sodium salt (11) (41 mg) was isolated as a brown non-crystalline powder.

EXAMPLE 5

This non-limiting Example illustrates the preparation of formulations of the compounds of the invention.

(a) Emulsifiable Concentrate

Compound No 10 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No 11 (5 parts by weight and "Dyapol" PT (1 part by weight) were added to an aqueous solution (94 parts by weight) of "Teric" N8 and the mixture was ball milled to produce a stable aqueous suspension which may be diluted with water to the required conclentraltion to give an aqueous suspension which may be diluted with water to the required concentration to give an aqueous suspension which may be applied by spraying. ("Dyapol" is a Trade mark and "Dyapol" PT is an anionic suspending agent; "Teric" N8 is a product of ethoxylation of nonylphenol.)

(c) Emulsifiable Concentrate

Compound No 10 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction.)

(d) Dispersible Powder

Compound No 10 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "aerosol" OT/B is a formulation of the dioctyl ester of sodium sulfosuccinic acid.)

(e) High Strength Concentrate

Compound No 10 (99 parts by weight), silica aerogel (0.5 parts by weight) and synthetic amorphous silica (0.5 parts by weight) were blended and ground in a hammer-mill to produce a powder having a particle size less than 200 microns.

(f) Dusting Powder

Compound No 10 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing surface active agent and/or oil, to give aqueous compositions of the required concentration which were used, as described in Examples 6 to 8, in the evaluation of the preemergence and post-emergence herbicidal activity of the compounds.

EXAMPLE 6

The pre-emergent herbicidal activity of the compounds of the invention formulated as described in Example 5 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 2 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants are as follows:

TABLE 2

| | | Pre-emergent Herbicidal Activity | | | | | | | | |
|---|---|---|---|---|---|---|---|---|---|---|
| Compound No | Application Rate (kg/ha) | TEST PLANT | | | | | | | | |
| | | Wh | Ot | Rg | Jm | B | P | Ip | Ms | Sf |
| 6 | 1.0 | 5 | 3 | 5 | 5 | 4 | 0 | 0 | 0 | 0 |
| 7 | 0.25 | 0 | 5 | 5 | 5 | 0 | 0 | 0 | 0 | 0 |
| 8 | 0.25 | 0 | 0 | 5 | 0 | 0 | 0 | 0 | 0 | 0 |

Wh Wheat
Ot Wild Oats
Rg Ryegrass
Jm Japanese millet
B Barley
P Peas
Ip Ipomea
Ms Mustard
Sf Sunflower

EXAMPLE 7

The post-emergent herbicidal activity of the compounds of the invention formulated as described in Example 5 was assessed by the following procedure.

The seeds of the test species werd sown in rows 2 cm deep in soil contained in seed boxes. The monocotyledonous plants and the dicotyledonous plants were down in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants are as follows:

TABLE 3

| | | Post-emergent Herbicidal Activity | | | | | | | | |
|---|---|---|---|---|---|---|---|---|---|---|
| Compound No | Application Rate (kg/ha) | TEST PLANT | | | | | | | | |
| | | Wh | Ot | Rg | Jm | B | P | Ip | Ms | Sf |
| 6 | 1.0 | 5 | 5 | 5 | 5 | 5 | 0 | 0 | 0 | 0 |
| 6 | 0.25 | 4 | 4 | 1 | 5 | 5 | — | — | — | — |
| 7 | 0.25 | 5 | 5 | 5 | 5 | 5 | 0 | 0 | 0 | 0 |
| 7 | 0.0625 | 5 | 5 | 5 | 5 | 5 | — | — | — | — |
| 7 | 0.03125 | 2 | 5 | 5 | 5 | 5 | — | — | — | — |
| 8 | 0.2525 | 5 | 5 | 5 | 5 | 5 | 0 | 0 | 0 | 0 |
| 8 | 0.0625 | 5 | 5 | 5 | 5 | 5 | — | — | — | — |
| 8 | 0.03125 | 4 | 4 | 5 | 5 | 5 | — | — | — | — |

Wh Wheat
Ot Wild Oats
Rg Ryegrass
Jm Japanese millet
B Barley
P Peas
Ip Ipomea
Ms Mustard
Sf Sunflower

EXAMPLE 8

The compounds were formulated for test by mixing an appropriate amount of 5 ml of an emulsion prepared by diluting 160 ml of a solution containing 21.9 g per liter of "Span" and 80 and 78.2 g per liter of "Tween" 20 in methylcyclohexanone to 500 with water. "Span" 80 is a Trade Mark for a surface-active agent comprising sorbitan monolaurate. "Tween" 20 is a Trade Mark for a surface-active agent comprising a condensate of sorbitan monolautrate with 20 molar proportions of ethylene oxide. Each 5 ml emulsion containing a test compound was then diluted to 40 ml with water and sprayed on to young pot plants (post-emergence test) of the species named in Table 4 below. Damage to test plants was assessed after 14 days on a scale of 0 to 5 wherein 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal camage was carried out after 21 days using the same scale of 0 to 5 as the post-emergence test. In both cases the degree of herbicidal damage was assessed by comparision with untreated control plants. The results are given in Table 4 below. A dash (—) means no experiment was carried out.

The names of the test plants were as follows:

TABLE 4

| | | Post-emergent Herbicidal Activity | | | | | | | | | | |
|---|---|---|---|---|---|---|---|---|---|---|---|---|
| Compound No | APPLICATION Method Rate (kg/ha) | TEST PLANT | | | | | | | | | | |
| | | Mz | Ww | Rc | Br | Av | Dg | Al | St | Ec | Sh | Ag |
| 6 | 0.20 | 5 | 4 | 5 | 5 | 4 | 2 | 1 | 5 | 5 | 3 | 4 |
| 6 | 0.10 | 5 | 4 | 4 | 5 | 4 | 1 | 1 | 2 | 5 | 1 | 1 |
| 7 | 0.20 | 4 | 4 | 3 | 4 | 4 | 4 | 4 | 5 | 5 | 5 | 4 |
| 7 | 0.10 | 4 | 3 | 2 | 4 | 4 | 4 | 4 | 5 | 5 | 4 | 4 |
| 7 | 0.05 | 1 | 1 | 0 | 3 | 3 | 4 | 3 | 3 | 4 | 1 | 1 |
| 7 | 0.02 | 0 | 0 | 0 | 2 | 0 | 3 | 1 | 2 | 3 | 1 | 1 |
| 8 | 0.20 | 5 | 4 | 3 | 5 | 4 | 4 | 4 | 5 | 5 | 5 | 4 |
| 8 | 0.10 | 5 | 3 | 1 | 4 | 4 | 4 | 4 | 4 | 4 | 5 | 4 |
| 8 | 0.05 | 3 | 0 | 0 | 3 | 2 | 3 | 2 | 4 | 4 | 1 | 2 |

Mz Maize
Ww Winter wheat
Rc Rice
Br Barley
Av *Avena fatua*
Dg *Digitaria sanguinalis*
Al *Alopecurus myosuroides*
St *Setaria viridis*
Ec *Echinochloa crus-galli*
Sh *Sorghum halepense*
Ag *Agropyron repens*

What is claimed is:

1. A compound of the Formula I:

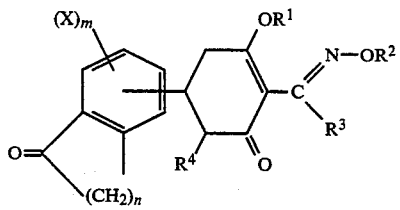

wherein:
m is zero or an integer selected from 1 to 3;
n is an integer selected from 2 to 4;
X, which may be the same or different, are independently selected from the group consisting of: halogen, $C_1$ to $C_6$ alkyl, $C_1$ to $C_6$ alkoxy and $C_1$ to $C_6$ alkylthio;
$R^1$ is selected from the group consisting of: hydrogen; $C_2$ to $C_6$ alkanoyl; benzoyl and substituted benzoyl wherein the benzene ring is substituted with from one to three substituents selected from the group consisting of halogens, nitro, $C_1$ to $C_6$ alkyl and $C_1$ to $C_6$ alkoxy; benzenesulfonyl and substituted benezenesulfonyl wherein the benzene ring is substituted with from one to three substituents selected from the group consisting of halogen, nitro, $C_1$ to $C_6$ alkyl and $C_1$ to $C_6$ alkoxy; and an inorganic or an organic cation selected from the alkali metals, the alkaline earth metals, the transition metals, the ammonium ion and the tri- and tetra(alkyl) ammonium ions wherein alkyl is selected from $C_1$ to $C_6$ alkyl and $C_1$ to $C_6$ hydroxyalkyl;
$R_2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl, $C_3$ to $C_6$ haloalkynyl; and substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, $C_1$ to $C_6$ alkyl, $C_1$ to $C_6$ haloalkyl, $C_1$ to $C_6$ alkoxy, and $C_1$ to $C_6$ alkylthio;
$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl; and
$R_4$ is selected from the group consisting of: hydrogen; halogen; cyano; $C_1$ to $C_6$ alkyl; and ($C_1$ to $C_6$ alkoxy) carbonyl.

2. A compound according to claim 1 wherein:
m is zero or an integer selected from 1 to 3;
n is an integer selected from 2 to 4;
X, which may be the same of different, are independently selected from the group consisting of: halogen, $C_1$ to $C_6$ alkyl, $C_1$ to $C_6$ alkoxy, and $C_1$ to $C_6$ alkylthio;
$R^1$ is selected from the group consisting of: hydrogen; $C^2$ to $C_6$ alkanoyl; benzoyl and substituted benzoyl wherein the benzene ring is substituted with from one to two substituents selected from the group consisting of halogen, nitro, $C_1$ to $C_6$ alkyl and $C_1$ to $C_6$ alkoxy; an alkali metal cation; an alkaline earth metal cation; a transition metal cation; the ammonium ion and the tri and tetra(alkyl) ammonium ions wherein alkyl is selected from $C_1$ to $C_6$ alkyl and $C_1$ to $C_6$ hydroxy-alkyl;

$R^2$ is selected from the group consisting of $C_1$ to $C_6$ alkyl, $C_1$ to $C_6$ haloalkyl, $C_2$ to $C_6$ alkenyl, $C_2$ to $C_6$ haloalkenyl and $C_3$ to $C_6$ alkynyl;

$R^3$ is selected from the group consisting of $C_1$ to $C_6$ alkyl;

$R^4$ is selected from the group consisting hydrogen, halogen, $C_1$ to $C_6$ alkyl; and ($C_1$ to $C_6$ alkoxy) carbonyl.

3. A compound according to claim 2 wherein:

m is zero or an integer selected from 1 to 3;

n is an integer selected from 2 to 4;

X, which may be the same or different, are independently selected from the group consisting of: halogen, $C_1$ to $C_6$ alkyl, $C_1$ to $C_6$ alkoxy, and $C_1$ to $C_6$ alkylthio;

$R^1$ is selected from the group consisting of: hydrogen; $C_2$ to $C_6$ alkanoyl; benzoyl; an alkali metal cation; an alkaline earth metal cation; a transition metal cation; the ammonium ion and the tri and tetra (alkyl) ammonium ions wherein alkyl is selected from $C_1$ to $C_6$ alkyl;

$R^2$ is selected from the group consisting of $C_1$ to $C_6$ alkyl, $C_1$ to $C_6$ haloalkyl, $C_2$ to $C_6$ alkenyl, $C_2$ to $C_6$ haloalkenyl and $C_3$ to $C_6$ alkynyl;

$R^3$ is selected from the group consisting of $C_1$ to $C_6$ alkyl; and $R^4$ is hydrogen.

4. A compound according to claim 3 wherein:

m is zero or an integer selected from 1 to 3;

n is an integer selected from 2 to 4;

X, which may be the same or different, are independently selected from the group consisting of: halogen, $C_1$ to $C_4$ alkyl, $C_1$ to $C_4$ alkoxy and $C_1$ to $C_4$ alkylthio;

$R^1$ is selected from the group consisting of: hydrogen; the alkali metal cations; the alkaline earth metal cations and the transition metal cations;

$R^2$ is selected from the group consisting of $C_1$ to $C_4$ alkyl, $C_1$ to $C_4$ haloalkyl, $C_2$ to $C_4$ alkenyl, $C_2$ to $C_4$ haloalkenyl and $C_3$ to $C_4$ alkynyl;

$R^3$ is selected from the group consisting of $C_1$ to $C_6$ alkyl; and $R^4$ is hydrogen.

5. A compound according to claim 4 wherein:

m is an integer selected from 1 to 3;

n is an integer selected from 2 to 4;

X, which may be the same or different, are independently selected from the group consisting of: $C_1$ to $C_4$ alkyl and $C_1$ to $C_4$ alkoxy;

$R^1$ is selected from the group consisting of hydrogen and the alkali metal cations;

$R^2$ is selected from the group consisting of $C_1$ to $C_4$ alkyl, $C_2$ to $C_4$ alkenyl, $C_2$ to $C_4$ haloalkenyl and $C_3$ to $C_4$ alkynyl;

$R^3$ is selected from $C_1$ to $C_4$ alkyl; and $R^4$ is hydrogen.

6. A compound according to claim 5 wherein:

m is an integer selected from 1 to 3;

n is an integer selected from 2 and 3;

X, which may be the same or different, are independently selected from the group consisting of methyl, ethyl, methoxy and ethoxy;

$R^1$ is selected from the group consisting of: hydrogen, and the sodium and potassium cations;

$R^2$ is selected from the group consisting of $C_1$ to $C_3$ alkyl, 2-haloethyl, allyl, 3-haloallyl and propargyl;

$R^3$ is selected from $C_1$ to $C_4$ alkyl; and $R^4$ is hydrogen.

7. A compound according to claim 6 wherein:

m is an integer selected from 2 and 3;

n is an integer selected from 2 and 3;

X, which may be the same or different, are independently selected from the group consisting of methyl and methoxy;

$R^1$ is selected from hydrogen and the sodium cation;

$R^2$ is selected from $C_1$ to $C_3$ alkyl, allyl and propargyl;

$R^3$ is selected from methyl, ethyl and n-propyl;

$R^4$ is hydrogen.

8. A compound according to claim 7 selected from the group consisting of:

5-(6,8-dimethyl-7-methoxy-1-oxo-1,2,3,4-tetrahydronaphth-5-yl)-2-[1-(ethoxyimino)propyl]-cyclohexana-1,3-dione;

5-(5,7-dimethyl-1-oxoindan-4-yl)-2-[1-(ethoxyimino)-propyl]cyclohexane-1,3-dione;

5-(5,7-dimethyl-1-oxoindan-6-yl)-2-[1-(ethoxyimino)-propyl]cyclohexane-1,3-dione;

5-(5,7-dimethyl-1-oxoindan-4-yl)-2-[1-(allyloxyimino)propyl]cyclohexane-1,3-dione;

5-(5,7-dimethyl-1-oxoindan-6-yl)-2-[1-(allyloxyimino)propyl]cyclohexane-1,3-dione.

9. A herbicidal composition comprising as active ingredient, a herbicidally effective amount of a compound as defined according to claim 1 and a carrier therefor.

10. A process for severely damaging or killing unwanted plants which process comprises applying to said plants, or to the growth medium of said plants, an effective amount of a compound as defined according to claim 1.

11. A process for selectively controlling the growth of monocotyledonous weeds in dicotyledonous crops which process comprises applying to said crop, or to the growth medium of said crop, a compound as defined according to claim 1 in an amount sufficient to severely damage or kill said weeds but insufficient to substantially damage said crop.

12. A process according to claim 10 to claim 11 wherein the compound is applied at a rate in the range of from 0.005 to 20 kilograms per hectare.

* * * * *